(12) United States Patent
Wick et al.

(10) Patent No.: US 11,587,232 B1
(45) Date of Patent: Feb. 21, 2023

(54) SYSTEMS AND METHODS FOR PREVENTING ERRORS IN MEDICAL IMAGING

(71) Applicants: CAMERAD TECHNOLOGIES, Decatur, GA (US); THE UAB RESEARCH FOUNDATION, Birmingham, AL (US)

(72) Inventors: Carson Arthur Wick, Atlanta, GA (US); Srini Tridandapani, Decatur, GA (US)

(73) Assignees: CAMERAD TECHNOLOGIES, Decatur, GA (US); THE UAB RESEARCH FOUNDATION, Birmingham, AL (US)

( * ) Notice: Subject to any disclaimer, the term of this patent is extended or adjusted under 35 U.S.C. 154(b) by 0 days.

(21) Appl. No.: 17/738,932

(22) Filed: May 6, 2022

(51) Int. Cl.
| | |
|---|---|
| *G06T 7/00* | (2017.01) |
| *G06F 3/16* | (2006.01) |
| *G10L 17/06* | (2013.01) |
| *G10L 17/04* | (2013.01) |
| *A61B 5/00* | (2006.01) |

(52) U.S. Cl.
CPC .......... *G06T 7/0016* (2013.01); *A61B 5/0035* (2013.01); *G06F 3/165* (2013.01); *G10L 17/04* (2013.01); *G10L 17/06* (2013.01); *G06T 2200/24* (2013.01); *G06T 2207/10016* (2013.01); *G06T 2207/30004* (2013.01)

(58) Field of Classification Search
CPC ......... G06F 3/165; G10L 17/04; G10L 17/06; G06T 7/0016; G06T 2200/24; G06T 2207/10016; G06T 2207/30004; A61B 5/0035
See application file for complete search history.

(56) References Cited

U.S. PATENT DOCUMENTS

| | | | |
|---|---|---|---|
| 9,355,309 B2 | 5/2016 | Tridandapani et al. | |
| 10,685,088 B2 * | 6/2020 | Ohashi | A61B 6/566 |

(Continued)

OTHER PUBLICATIONS

Tridandapani et al. "Initial experience with patient visible light images obtained simultaneously with portable radiographs." AJR. American journal of roentgenology 214.1 (2020): 68. (Year: 2020).*

(Continued)

*Primary Examiner* — Katrina R Fujita
(74) *Attorney, Agent, or Firm* — Workman Nydegger

(57) ABSTRACT

A method for preventing wrong-patient errors includes receiving a selection of a current imaging subject. The current imaging subject is selected for a current image acquisition session comprising capturing one or more current images of the current imaging subject utilizing at least a first image sensor system of a first imaging modality. The method includes accessing one or more previous images of a previous imaging subject. The one or more previous images depict the previous imaging subject according to at least a second imaging modality that is different from the first imaging modality. The method includes presenting the one or more previous images on a display system and, in response to determining that the previous imaging subject matches the current imaging subject based upon the one or more previous images, performing the current image acquisition session.

15 Claims, 10 Drawing Sheets

(56) References Cited

U.S. PATENT DOCUMENTS

| | | | | |
|---|---|---|---|---|
| 2005/0109350 | A1* | 5/2005 | Luloh | A61B 90/90 128/898 |
| 2006/0109957 | A1* | 5/2006 | Lutjens | A61B 6/4441 378/205 |
| 2007/0192133 | A1* | 8/2007 | Morgan | G16H 30/20 600/300 |
| 2012/0050321 | A1* | 3/2012 | Arieli | A61B 6/5247 345/629 |
| 2013/0177222 | A1* | 7/2013 | Tridandapani | A61B 5/117 382/128 |
| 2013/0317854 | A1* | 11/2013 | Winder | G16H 30/20 705/3 |
| 2014/0032222 | A1* | 1/2014 | Vetter | G16H 10/65 704/274 |
| 2014/0350381 | A1* | 11/2014 | Kim | A61M 5/16831 600/431 |
| 2018/0182478 | A1* | 6/2018 | Liebscher | G16H 10/60 |
| 2020/0219255 | A1* | 7/2020 | Wick | G16H 40/67 |
| 2021/0271931 | A1* | 9/2021 | Younis | G16H 30/20 |

OTHER PUBLICATIONS

"A Scientific Computing Framework for Luajit", Torch, Retrieved from http://torch.ch/, Retrieved on Sep. 1, 2022, 2 Pages.
"About us", IMV, Retrieved from https://imvinfo.com/about-us/, Retrieved on Sep. 2022, 1 Page.
"Applying the Universal Protocol to Improve Patient Safety in Radiology Services", Pennsylvania Patient Safety Advisory, vol. 8, No. 2, Jun. 2011, 8 Pages.
"Crossing the Quality Chasm: A New Health System for the 21st Century", Committee on Quality of Health Care in America, Institute of Medicine, 2001, 360 Pages.
"Data Analysis Tool", National Practitioner Data Bank, U.S. Department of Health & Human Services, Retrieved from https://www.npdb.hrsa.gov/index.jsp, Retrieved on Sep. 2022, 1 Page.
"Doctor Receives Reprimand From State for Removing Wrong Man's Kidney", Retrieved from https://www.nbcboston.com/, Jan. 24, 2019, 2 pages.
"From Research To Production", PyTorch, Retrieved from https://pytorch.org/, Retrieved on Sep. 1, 2022, 4 Pages.
"Global Diagnostic Medical Imaging Market Huge Growth Opportunities, Trends and Forecast to 2025—QY Research, Inc. ", Retrieved from http://www.sbwire.com/press-releases/global-diagnostic-medical-imaging-market-huge-growth-opportunities-trends-and-forecast-to-2025-qy-research-inc-1033623.htm, Aug. 2018, 5 Pages.
"Hospital National Patient Safety Goals", The Joint Commission Accreditation Hospital, 2017, Retrieved from https://www.jointcommission.org/-/media/tjc/documents/standards/national-patient-safety-goals/historical/2017_npsg_hap_erpdf.pdf?db=web&hash=08B0E173E6DB13140B6F719E5FB069FE&hash=08B0E173E6DB13140B6F719E5FB069FE, Retrieved on Sep. 2022, 1 Page.
"National highway traffic safety administration", Retrieved from https://www-fars.nhtsa.dot.gov/Main/index.aspx, Retrieved on Sep. 2022, 1 Page.
"OpenFace", Retrieved from https://cmusatyalab.github.io/openface/, Retrieved on Sep. 1, 2022, 3 Pages.
"Safe Practices for Better Healthcare—2010 Update", A Consensus Report, National Quality Forum, 2010, 466 pages.
"Timesler/facenet-pytorch", GitHub, Retrieved from https://github.com/timesler/facenet-pytorch, Retrieved on Sep. 1, 2022, 14 Pages.
Boonn et al., "Radiologist Use of and Perceived Need for Patient Data Access", J Digit Imaging. Aug. 2009; 22(4):357-362.
James J.T, "A New, Evidence-based Estimate of Patient Harms Associated with Hospital Care", J Patient Saf, vol. 9, No. 3, Sep. 2013, pp. 122-128.
Lacson et al., "Integrity of clinical information in computerized order requisitions for diagnostic imaging", Journal of the American Medical Informatics Association, 25(12), 2018, 1651-1656.
Maes et al., "Medical Image Registration Using Mutual Information", Proceedings of the IEEE, vol. 91, Issue: 10, Oct. 2003, 24 Pages.
Ozeke et al., "Second victims in health care: current perspectives", Advances in Medical Education and Practice, Adv Med Educ Pract, Aug. 12, 2019;10: pp. 593-603.
Phipps et al., "He Thought the "Lady in the Door" Was the "Lady in the Window": A Qualitative Study of Patient Identification Practices", The Joint Commission Journal on Quality and Patient Safety, vol. 38 No. 3, Mar. 2012, pp. 127-134.
Ramamurthy et al., "A Novel Technology for Automatically Obtaining Digital Facial Photographs Near-Simultaneously with Portable Radiographs", J Digit Imaging, Jun. 2015; 28(3): 259-63.
Ramamurthy et al., "Integrating Patient Digital Photographs with Medical Imaging Examinations", J Digit Imaging. Oct. 2013; 26(5): 875-885.
Sadigh et al., "Evaluation of Near-Miss Wrong-Patient Events in Radiology Reports", Health Care Pol icy and Quality Original Research, AJR Am J Roentgenol ,205(2) Aug. 2015, pp. 337-343.
Sadigh et al., "Stakeholders' Perceptions Regarding the Use of Patient Photographs Integrated with Medical Imaging Studies", J Digit Imaging, Jun. 2016; 29(3), pp. 341-346.
Schroff et al., "FaceNet: A Unified Embedding for Face Recognition and Clustering", 2015 IEEE Conference on Computer Vision and Pattern Recognition (CVPR), 2015, 9 Pages.
Schultz et al., "Patient Safety Event Reporting in a Large Radiology Department", Sep. 2011, American Journal of Roentgenology , vol. 197, No. 3, pp. 684-688.
Thornton et al., "Analysis and Prioritization of Near-Miss Adverse Events in a Radiology Department", AJR Am J Roentgenol, May 2011; 196(5):1120-1124.
Tridandapani et a., "A Multi-observer Study of the Effects of Including Point-of-care Patient Photographs with Portable Radiography: A Means to Detect Wrong-Patient Errors", Acad Radiol. Aug. 2014; 21(8): 1038-1047.
Tridandapani et al., "Improvement in Detection of Wrong-Patient Errors When Radiologists Include Patient Photographs in Their Interpretation of Portable Chest Radiographs", J Digit Imaging. Dec. 2015; 28(6): 664-670.
Tridandapani et al., "Increasing Rate of Detection of Wrong-Patient Radiographs: Use of Photographs Obtained at Time of Radiography", AJR Am J Roentgenol, Apr. 2013; 200(4): W345-52, 16 Pages.
Tridandapani et al., "Interpreting Radiographs with Concurrently Obtained Patient Photographs", Radio Graphics 2019; vol. 39, 1356-1367.
Zygmont et al., "Using Point-of-Care Patient Photographs With Musculoskeletal Radiography to Identify Errors of Laterality in Emergency Department Imaging", Curr Probl Diagn Radiol, Nov.-Dec. 2021; 50(6), pp. 787-791.

* cited by examiner

700

702 Receiving A Selection Of A Current Imaging Subject, The Current Imaging Subject Being Selected For A Current Image Acquisition Session Comprising Capturing One Or More Current Images Of The Current Imaging Subject Utilizing At Least A First Image Sensor System Of A First Imaging Modality

704 Accessing A Set Of One Or More Previous Images Of A Previous Imaging Subject, The One Or More Previous Images Depicting The Previous Imaging Subject According To At Least A Second Imaging Modality That Is Different From The First Imaging Modality

706 Presenting The One Or More Previous Images On A Display System

708 In Response To Determining That The Previous Imaging Subject Matches The Current Imaging Subject Based Upon The One Or More Previous Images Of The Second Imaging Modality, Performing The Current Image Acquisition Session By Capturing The One Or More Current Images Of The Current Imaging Subject Utilizing At Least The First Image Sensor System Of The First Imaging Modality

710 Associating The One Or More Current Images With The Previous Imaging Subject Within A Subject Data Repository

```
                                                              ┌─ 802
┌─────────────────────────────────────────────────────────────────┐
│ Receiving A Selection Of A Current Imaging Subject, The Current │
│ Imaging Subject Being Selected For A Current Image Acquisition  │
│ Session Comprising Capturing One Or More Current Images Of The  │
│ Current Imaging Subject Utilizing At Least A First Image Sensor │
│              System Of A First Imaging Modality                 │
└─────────────────────────────────────────────────────────────────┘
                              │
                              ▼                          ┌─ 804
┌─────────────────────────────────────────────────────────────────┐
│  Accessing One Or More Previous Audio Recordings Or One Or More │
│        Voice Signatures Of A Previous Imaging Subject           │
└─────────────────────────────────────────────────────────────────┘
                              │
                              ▼                          ┌─ 806
┌─────────────────────────────────────────────────────────────────┐
│ In Response To Determining That The Previous Imaging Subject    │
│ Matches The Current Imaging Subject Based Upon The One Or More  │
│ Previous Audio Recordings Or The One Or More Voice Signatures,  │
│ Performing The Current Image Acquisition Session By Capturing   │
│ The One Or More Current Images Of The Current Imaging Subject   │
│ Utilizing At Least The First Image Sensor System Of The First   │
│                        Imaging Modality                         │
└─────────────────────────────────────────────────────────────────┘
```

SYSTEMS AND METHODS FOR PREVENTING ERRORS IN MEDICAL IMAGING

STATEMENT REGARDING FEDERALLY SPONSORED RESEARCH

The invention was made with government support under Award #1853142 SBIR Phase II: Point-of-Care Patient Photography Integrated with Medical Imaging awarded by the National Science Foundation. The government may have certain rights in the invention.

BACKGROUND

Advances in computing technology have resulted in a concomitant advance in medical device technologies, including within the field of diagnostic medicine. Particularly, the past century has demonstrated significant advances in medical imaging devices. Such advances have been hallmarked by the improvement and advent of new radiologic devices, such as radiography, computed tomography (CT), magnetic resonance imaging (MRI), and other radiologic imaging systems that allow for the non-invasive viewing and exploration of internal structures of the body. These medical imaging technologies allow physicians and clinicians to better document, diagnose, and treat pathologies.

Unfortunately, medical imaging studies are prone to mislabeling, such as associating the wrong demographic information (e.g., a different patient's name and medical record number) to a patient's imaging examination. Patient misidentification errors in medical imaging can result in serious consequences, such as the misdiagnosis of a disease state or the application of an inappropriate treatment regimen. Furthermore, the failure to properly associate a medical image study and patient identification may propagate to future imaging studies and negatively affect patient management decisions.

For example, an exemplary wrong-patient error case is illustrated in FIGS. 1A and 1B. The radiograph illustrated in FIG. 1A is a radiograph obtained from a 43-year old black male following coronary artery bypass grafting and who has a left ventricular assist device and an implantable defibrillator. The patient presented with heart failure, and the healthcare personnel recruited to evaluate this radiograph presumed the radiograph illustrated in FIG. 1B to be a radiograph from the same patient captured at an earlier timepoint. However, the radiograph of FIG. 1B is actually a radiograph of a 64-year old white male who had undergone bilateral lung volume reduction surgery for chronic obstructive pulmonary disease. The radiograph of FIG. 1B was intentionally mislabeled as an earlier radiograph of the patient illustrated in the radiograph of FIG. 1A. When presented to seasoned radiologists for diagnosis, 4 out of 4 readers failed to identify the mislabeling error and assumed that the patient had suffered a myocardial infarction and complications from surgery in the interim. In general, the nature of radiologic planar and cross-sectional images makes it difficult to correctly correlate radiologic medical images with patient details absent other identifying characteristics. As in the foregoing example, obvious age and racial differences between the patients of the mislabeled radiographs were completely lost or unobservable within the radiologic images, making it difficult for radiologists to identify the error.

Accordingly, there is a need to minimize or prevent mislabeling of radiologic images.

The subject matter described herein is not limited to embodiments that solve any disadvantages or that operate only in environments such as those described above. Rather, this background is only provided to illustrate one exemplary technology area where some embodiments described herein may be practiced.

BRIEF SUMMARY

Disclosed embodiments are directed to systems, devices, and methods for preventing errors in medical imaging (e.g., wrong-patient errors, laterality errors).

In one aspect, a computer-implemented method for preventing wrong-patient errors includes receiving a selection of a current imaging subject. The current imaging subject is selected for a current image acquisition session comprising capturing one or more current images of the current imaging subject utilizing at least a first image sensor system of a first imaging modality. The computer-implemented method further includes accessing a set of one or more previous images of a previous imaging subject. The one or more previous images of the previous imaging subject are associated with one or more image capture timepoints that temporally precede the current image acquisition session. The one or more previous images depict the previous imaging subject according to at least a second imaging modality that is different from the first imaging modality. The computer-implemented method further includes presenting the one or more previous images on a display system and, in response to determining that the previous imaging subject matches the current imaging subject based upon the one or more previous images of the second imaging modality, performing the current image acquisition session by capturing the one or more current images of the current imaging subject utilizing at least the first image sensor system of the first imaging modality.

In one aspect, a computer-implemented method for preventing wrong-patient errors includes receiving a selection of a current imaging subject. The current imaging subject is selected for a current image acquisition session comprising capturing one or more current images of the current imaging subject utilizing at least a first image sensor system of a first imaging modality. The computer-implemented method further includes accessing one or more previous audio recordings or one or more voice signatures of a previous imaging subject, and, in response to determining that the previous imaging subject matches the current imaging subject based upon the one or more previous audio recordings or the one or more voice signatures, performing the current image acquisition session by capturing the one or more current images of the current imaging subject utilizing at least the first image sensor system of the first imaging modality.

In one aspect, a computer-implemented method for preventing laterality errors includes capturing one or more images of a structure and accessing an indication of one or more intended structure attributes. The one or more intended structure attributes are selected to be embodied by the structure imaged during a current image acquisition session. The computer-implemented method further includes determining one or more imaged structure attributes by utilizing the one or more images of the structure as input to one or more artificial intelligence modules configured to determine structure attributes based upon input imagery. The one or more imaged structure attributes comprise output of the one or more artificial intelligence modules. The computer-implemented method further includes, in response to determining one or more discrepancies between the one or more imaged structure attributes and the one or more intended structure attributes, presenting a notification on a user interface.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims or may be learned by the practice of the invention as set forth hereinafter.

BRIEF DESCRIPTION OF THE DRAWINGS

In order to describe the manner in which the above recited and other advantages and features of the disclosure can be obtained, a more particular description of the disclosure briefly described above will be rendered by reference to specific embodiments thereof, which are illustrated in the appended drawings. It is appreciated that these drawings depict only typical embodiments of the disclosure and are not therefore to be considered to be limiting of its scope. The disclosure will be described and explained with additional specificity and detail through the use of the accompanying drawings in which:

FIG. 7, FIG. 8, and FIG. 9 illustrate example flow diagrams depicting acts associated with preventing errors in medical imaging.

DETAILED DESCRIPTION

Figure 1A:
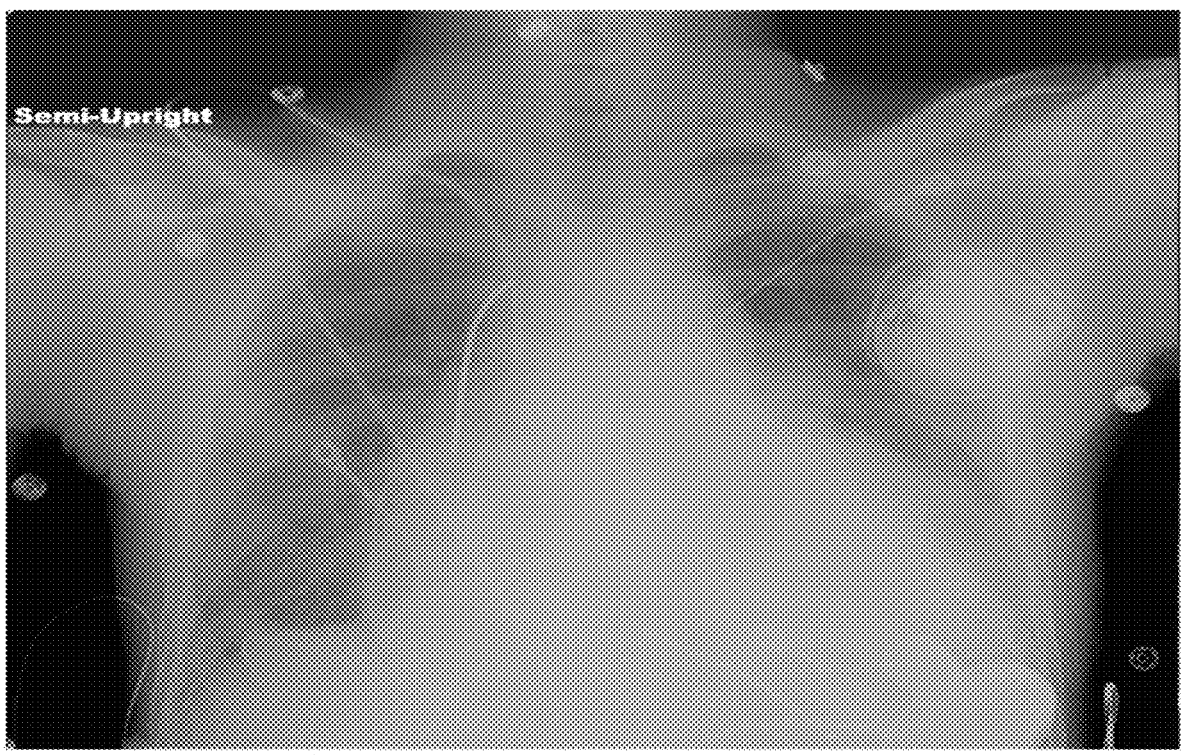
FIG. 1A and FIG. 1B illustrate radiographs within a simulated wrong-patient error case.
Figure 1B:
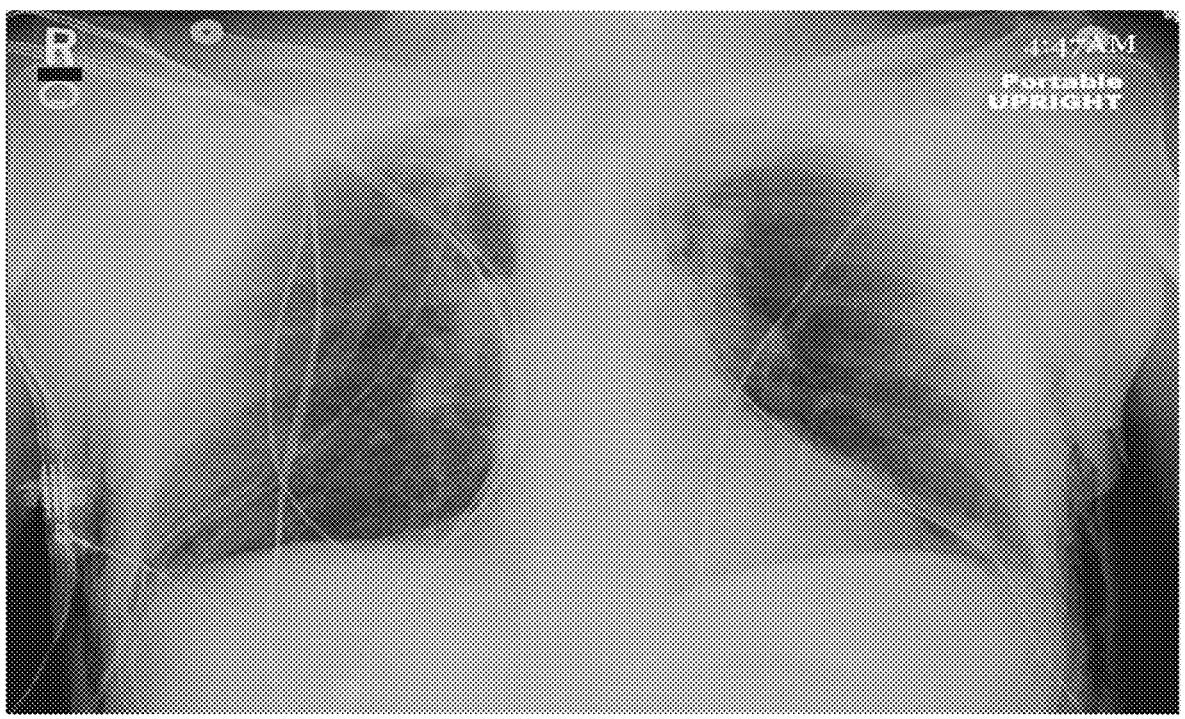

Before describing various embodiments of the present disclosure in detail, it is to be understood that this disclosure is not limited to the parameters of the particularly exemplified systems, methods, apparatus, products, processes, and/or kits, which may, of course, vary. Thus, while certain embodiments of the present disclosure will be described in detail, with reference to specific configurations, parameters, components, elements, etc., the descriptions are illustrative and are not to be construed as limiting the scope of the claimed invention. In addition, the particular example terminology used herein is for the purpose of describing the embodiments and is not necessarily intended to limit the scope of the claimed invention.

As noted above, despite the numerous advances made in the field of medical imaging, wrong-patient errors still occur (e.g., where a medical imaging study of one patient becomes associated with an incorrect patient who is/was not the subject of the imaging study). Various protocols exist for reducing wrong-patient errors, such as requiring verification of at least two patient identifiers when radiologic images are being obtained. Various patient identifiers may be used, such as name, date of birth, social security number, hospital/institution registration number, and/or others. However, such verification protocols are susceptible to many different types of shortcomings/errors. For example, such verification may not always be possible, including with, for example, many trauma patients, patients who are unconscious or mentally unsound, infants etc. Furthermore, even if a technologist correctly gathers the requisite identifiers, it is difficult to verify with certainty that the identifiers have been properly associated with the patient. For example, the patient may have been given a mislabeled identification bracelet, or some other mislabeling error could occur before or after the point-of-care verification, which can lead to errors in the canonical multi-parameter verification process.

As noted above, wrong-patient errors can lead to numerous undesirable outcomes. For example, in the context of medical imaging, a medical imaging technologist may intend to conduct a medical imaging study of an intended patient for whom a previous medical imaging study was conducted (e.g., to facilitate longitudinal, multi-timepoint analysis of a medical condition of the intended patient). Various errors may occur causing the technologist to conduct the medical imaging study on a different patient who is different than the intended patient. The resulting medical imagery of the different patient may become wrongly associated with the intended patient, causing a wrong-patient error. If the wrong-patient error is not subsequently detected, treatment or other decisions for the intended patient may be wrongly influenced by the images depicting the different patient. Even if the wrong-patient error is then subsequently identified in a retroactive manner, the different patient may have been unnecessarily exposed to harmful radiation associated with the medical imaging, and costs associated with unnecessarily running/operating the medical imaging equipment may be wasted.

The present disclosure relates at least to systems, methods, and devices for preventing wrong-patient errors. The embodiments disclosed herein may be implemented at the point of medical image acquisition, or prior to the point of medical image acquisition, to enable pro-active prevention of wrong-patient errors. By proactively preventing wrong-patient errors from being stored or recorded within patient databases, the disclosed embodiments may prevent many of the inefficiencies and dangers associated with reliance on wrong associations between medical images (and/or other medical information) and patients (e.g., unnecessary radiation exposure, waste of imaging resources/time, medical misdiagnosis, medical mistreatment, and/or others).

At least some disclosed embodiments are directed to preventing wrong-patient errors by presenting previous-timepoint imagery of a patient selected for a current imaging study. The previous-timepoint imagery may be associated with the identity of the selected patient within a patient database. For example, the previous-timepoint imagery may have been captured and stored in association with the identity of the selected patient during a previous imaging study of the selected patient. The previous timepoint imagery may comprise one or more images of a different modality than the modality/modalities of at least some of the imagery to be captured via the current imaging study. For example, the previous-timepoint imagery may comprise visible-light imagery (e.g., RGB imagery, and/or other imagery such as ultrasound imagery), whereas the current imaging study may include capturing radiograph images of the patient.

The previous-timepoint imagery may be presented to a medical imaging technologist to allow the technologist to ascertain whether the patient currently present with the technologist corresponds to the patient selected for the current imaging study. If the technologist determines that the current patient and the selected patient match, the technologist may proceed with the imaging study, and the newly captured images of the selected patient may be properly associated with the patient's identity within a database. If the technologist determines that the current patient and the selected patient do not match, the technologist may refrain from imaging the current patient, thereby refraining from unnecessarily exposing the current patient to potentially harmful radiation and preventing downstream errors that might result from storing the captured imagery in association with the selected patient.

At least some disclosed embodiments are directed to preventing wrong-patient errors based upon previous-timepoint audio recordings of a patient selected for a current imaging study. The previous-timepoint audio recordings may be associated with the identity of the selected patient within a patient database. In some instances, the previously captured audio recording(s) may be presented to a technologist prior to commencing the current imaging study to allow the technologist to compare the previously recorded audio for the selected patient to vocalizations of the patient who is currently present with the technologist, thereby allowing the technologist to ascertain whether the patient currently before them corresponds to the patient selected for the current imaging study. If the technologist determines that the current patient and the selected patient match, the technologist may proceed with the imaging study, and the newly captured images of the selected patient may be properly associated with the patient's identity within a database (the newly captured image(s) may include video and/or accompanying audio). If the technologist determines that the current patient and the selected patient do not match, the technologist may refrain from imaging the current patient, thereby refraining from unnecessarily exposing the current patient to potentially harmful radiation and preventing downstream errors that might result from storing the captured imagery in association with the selected patient.

In some instances, previous-timepoint audio recordings are utilized to generate a voice signature or voiceprint for a selected patient, and the voice signature or voiceprint is associated with the identity of the selected patient within a patient database. To determine whether a patient physically present for an imaging study corresponds to a patient selected for a current imaging study, the physically present patient may be prompted to speak, and their vocalization(s) may be recorded and assessed against the voice signature or voiceprint (e.g., via a voice authentication operation) stored for the selected patient to determine whether the physically present patient corresponds to the selected patient. If the identity of the physically present patient matches the identity of the selected patient based upon the voice authentication, the imaging study of the physically present patient may proceed. If the identity of the physically present patient does not match the identity of the selected patient based upon the voice authentication, the imaging study of the physically present patient may be prevented.

Some embodiments are directed to preventing medical imaging errors associated with capturing and/or storing medical imagery of incorrect patient bodily structures. Such errors often occur in the form of wrong-side errors or laterality errors, where a bodily structure associated with a particular side of a patient's body is intended for medical imaging (e.g., a patient's left arm), but a bodily structure associated with the other side of the patient's body becomes medically imaged (e.g., the patient's right arm).

Accordingly, at least some disclosed embodiments are directed to capturing initial images of a patient's bodily structure that is targeted for a medical imaging study. The initial images may be captured utilizing visible light image sensors and/or other image sensor types that do not subject the imaged structure to harmful radiation. Image data of the initial images may be processed utilizing one or more artificial intelligence modules (e.g., convolutional neural networks) to determine imaged structure attributes of the patient's bodily structure, such as laterality of the structure. The imaged structure attributes may be compared to intended structure attributes for the medical imaging study. The intended structure attributes may be obtained, for example, from a medical imaging request, schedule, queue, etc. If the imaged structure attributes correspond to the intended structure attributes (e.g., indicating that laterality of the targeted bodily structure matches the intended structure laterality for medical imaging), the medical imaging study of the targeted bodily structure may proceed. If the imaged structure attributes fail to correspond to the intended structure attributes (e.g., indicating that laterality of the targeted bodily structure does not match the intended structure laterality for medical imaging), the medical imaging of the targeted bodily structure may be prevented.

Having just described some various high-level features and benefits of the disclosed embodiments, attention will now be directed to FIGS. 2 through 9. These Figures illustrate various conceptual representations, components, architectures, methods, and supporting illustrations related to the disclosed embodiments.

Example Systems and Techniques for Preventing Errors in Medical Imaging

Figure 2:
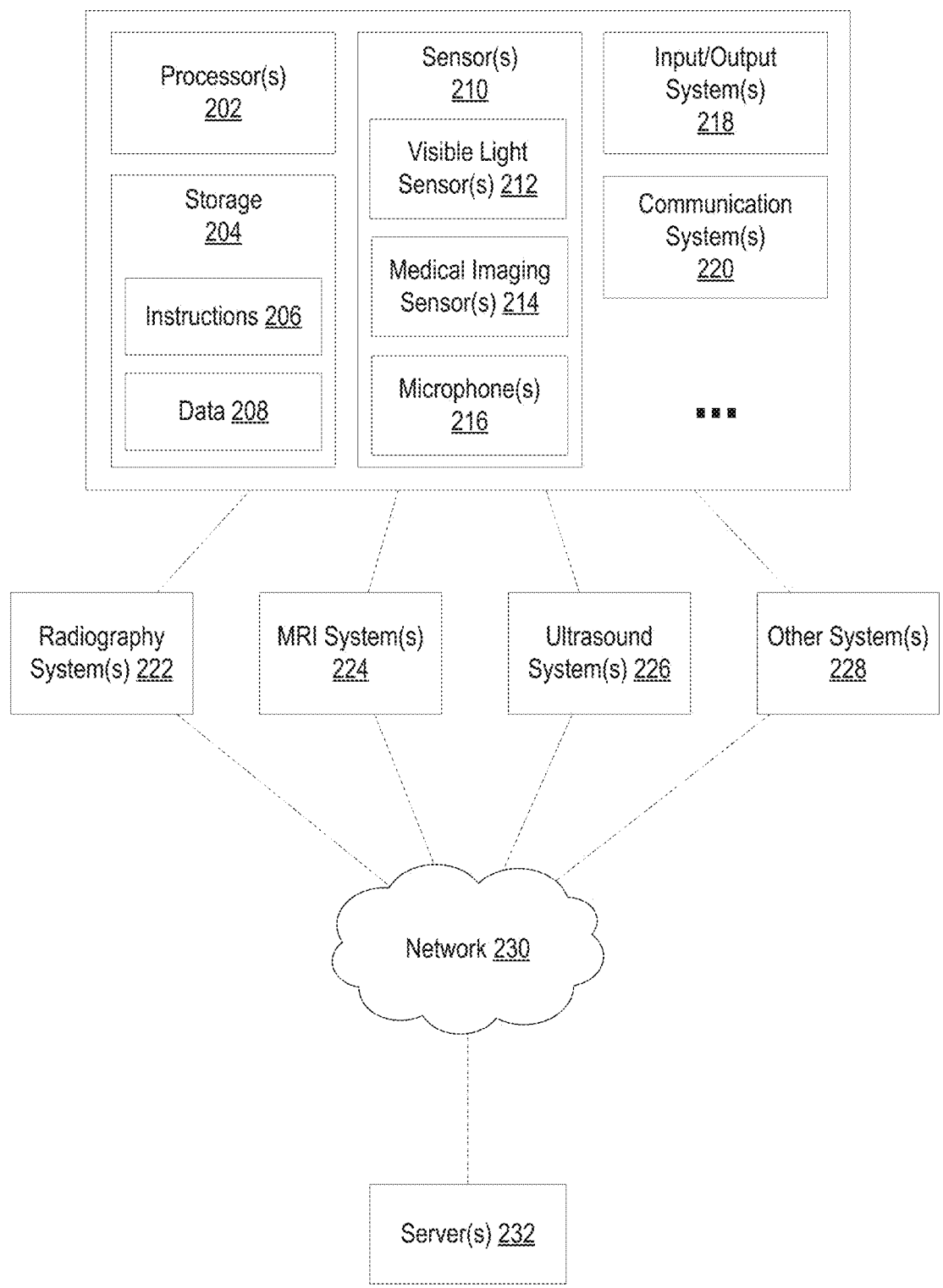
FIG. 2 illustrates example components of example systems that may comprise or implement the disclosed embodiments.

FIG. 2 illustrates example components of example systems that may comprise or implement the disclosed embodiments. For example, the components illustrated in FIG. 2 include processor(s) 202, storage 204, sensor(s) 210, input/output system(s) 218 (I/O system(s) 218), and communication system(s) 220. Although FIG. 2 illustrates particular components, one will appreciate, in view of the present disclosure, that systems for implementing the disclosed embodiments may comprise any number of additional or alternative components (as indicated by the ellipsis).

The processor(s) 202 may comprise one or more sets of electronic circuitries that include any number of logic units, registers, and/or control units to facilitate the execution of computer-interpretable instructions (e.g., instructions that form a computer program). Such computer-interpretable instructions may be stored within storage 204. The storage 204 may comprise physical system memory and may be volatile, non-volatile, or some combination thereof. Furthermore, storage 204 may comprise local storage, remote storage (e.g., accessible via communication system(s) 220 or otherwise), or some combination thereof. Additional details related to processors (e.g., processor(s) 202) and computer storage media (e.g., storage 204) will be provided hereinafter.

In some implementations, the processor(s) 202 may comprise or be configurable to execute any combination of software and/or hardware components that are operable to facilitate processing using machine learning models or other artificial intelligence-based structures/architectures. For example, processor(s) 202 may comprise and/or utilize hardware components or computer-executable instructions operable to carry out function blocks and/or processing layers configured in the form of, by way of non-limiting example, single-layer neural networks, feed forward neural networks, radial basis function networks, deep feed-forward networks, recurrent neural networks, long-short term memory (LSTM) networks, gated recurrent units, autoencoder neural networks, variational autoencoders, denoising autoencoders, sparse autoencoders, Markov chains, Hopfield neural networks, Boltzmann machine networks, restricted Boltzmann machine networks, deep belief networks, deep convolutional networks (or convolutional neural networks), deconvolutional neural networks, deep convolutional inverse graphics networks, generative adversarial networks, liquid state machines, extreme learning machines, echo state networks, deep residual networks, Kohonen networks, support vector machines, neural Turing machines, and/or others.

As will be described in more detail, the processor(s) 202 may be configured to execute instructions 206 stored within storage 204 to perform certain actions associated with preventing errors in medical imaging. The actions may rely at least in part on data 208 stored on storage 204 in a volatile and/or non-volatile manner.

In some instances, the actions may rely at least in part on communication system(s) 220 for receiving data from remote system(s), which may include, for example, separate systems or devices, sensors, servers, cloud resources/services, and/or others. The communications system(s) 220 may comprise any combination of software or hardware components that are operable to facilitate communication between on-system components/devices and/or with off-system components/devices. For example, the communications system(s) 220 may comprise ports, buses, or other physical connection apparatuses for communicating with other devices/components. Additionally, or alternatively, the communications system(s) 220 may comprise systems/components operable to communicate wirelessly with external systems and/or devices through any suitable communication channel(s), such as, by way of non-limiting example, Bluetooth, ultra-wideband, WLAN, infrared communication, and/or others.

FIG. 2 illustrates that a system for implementing the disclosed embodiments may comprise or be in communication with I/O system(s) 218. I/O system(s) 218 may include any type of input or output device such as, by way of non-limiting example, a touch screen, a mouse, a keyboard, a controller, and/or others, without limitation. For example, the I/O system(s) 218 may include a display system that may comprise any number of display panels, optics, laser scanning display assemblies, and/or other components.

Furthermore, FIG. 2 illustrates that a system for implementing the disclosed embodiments may comprise or be in communication with sensor(s) 210. Sensor(s) 210 may comprise any device for capturing or measuring data representative of perceivable or detectable phenomena. By way of non-limiting example, the sensor(s) 210 may comprise one or more image sensors, microphones (e.g., microphone(s) 216), thermometers, barometers, magnetometers, accelerometers, gyroscopes, and/or others. FIG. 2 indicates that various types of image sensors are within the scope of the present disclosure. For instance, FIG. 2 depicts that the sensor(s) 210 may comprise visible light sensor(s) 212 and medical imaging sensor(s) 214. Visible light sensor(s) 212 may comprise charge-coupled device (CCD) image sensors, complementary metal-oxide-semiconductor (CMOS) image sensors, single photon avalanche diode (SPAD) image sensors, and/or any other type of image sensor configured to detect photons within (but not limited to) at least a portion of the visible spectrum (e.g., between about 380 nm and about 750 nm) to capture imagery (e.g., intensity or grayscale images, RGB images, and/or others).

Medical imaging sensor(s) 214 may comprise any type of device for capturing images of patients within a medical use context (e.g., medical assessment/diagnostic purposes, treatment assessment purposes, etc.). Medical imaging sensor(s) 214 may include, by way of non-limiting example, radiography devices (e.g., x-ray devices, computed tomography (CT) devices, positron emission tomography (PET) devices, nuclear medicine imaging devices, and/or others), magnetic resonance imaging (MM) devices, ultrasound devices, and/or others.

The components shown in FIG. 2 may be implemented in various types and/or combinations of systems/devices to facilitate prevention of medical imaging errors in accordance with the present disclosure. For example, any number of the components discussed hereinabove with reference to FIG. 2 may be implemented in association with radiography system(s) 222, Mill system(s) 224, ultrasound system(s) 226, and/or other system(s) 228. For example, radiography system(s) 222 may be implemented in the form of a portable digital radiography (DR) machine, with visible light sensor(s) 212 coupled to the medical imaging sensor(s) 214 components of the DR machine.

Figure 3:
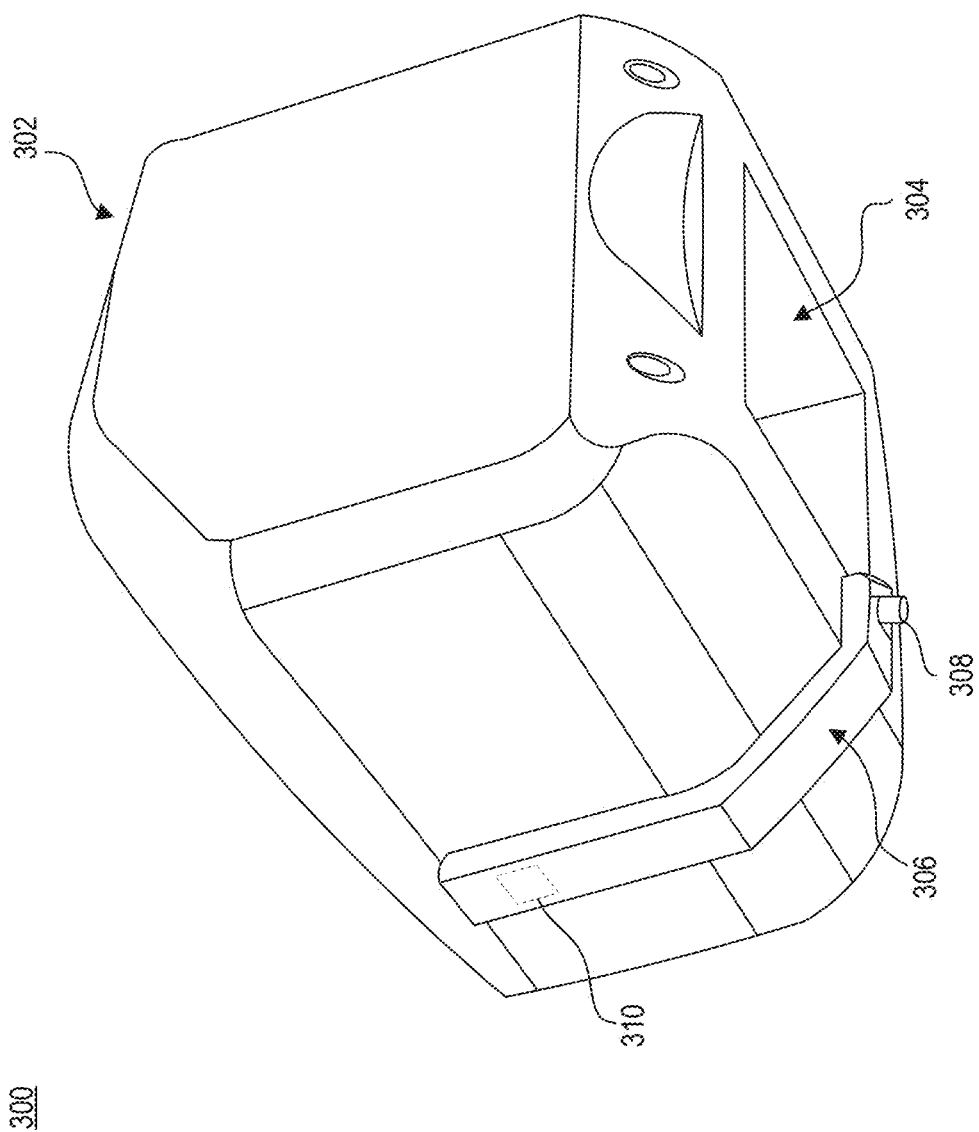
FIG. 3 illustrates an example visible spectrum image sensor coupled to a medical image sensor.

Attention is briefly directed to FIG. 3, which illustrates an example isolated representation of an X-ray head 302 of a portable DR machine 300 (other components such as wires, handles, etc. are omitted for clarity). The portable DR machine 300 may comprise a radiography system 222 as discussed hereinabove with reference to FIG. 2. The X-ray head 302 includes an X-ray source 304 for emitting X-ray radiation to facilitate radiograph acquisition. The X-ray source 304 (combined with an X-ray detector) may comprise medical imaging sensor(s) 214 as described above with reference to FIG. 2. FIG. 3 also illustrates an example camera system 306 associated with the portable DR machine 300. The camera system 306 includes an image sensor 308 (e.g., visible light sensor(s) 212, discussed hereinabove with reference to FIG. 2) and a camera controller 310 (e.g., processor(s) 202 and/or storage 204, discussed hereinabove with reference to FIG. 2) to facilitate photograph and/or video acquisition (the camera system 306 may accordingly comprise or be associated with one or more microphones to capture audio to accompany acquired video).

FIG. 3 illustrates the camera system 306 is mounted or coupled to the X-ray head 302, thereby enabling easy use of the camera system 306 in conjunction with the X-ray head 302. For example, a medical imaging session may include capturing visible light images of a patient (utilizing the camera system 306) before, substantially contemporaneous with, or after capturing X-ray images of the patient (utilizing the X-ray source 304 and an X-ray detector).

Although not illustrated in FIG. 3, a portable DR machine 300 may additionally or alternatively be associated with microphone(s) 216. The microphone(s) 216 may be mounted to the X-ray head 302, to another portion of the portable DR machine 300, or be uncoupled from the portable DR machine 300. In some instances, the microphone(s) 216 is/are part of the camera system 306. The microphone(s) 216 may enable audio recordings of a patient to be captured before, contemporaneous with, or after capturing of medical images of the patient pursuant to a medical imaging session for the patient.

One will appreciate, in view of the present disclosure, that visible light sensor(s) 212 may be mounted to, coupled with, or otherwise integrated into or associated with other types of medical imaging sensors, such as CT devices, MRI devices, ultrasound devices, etc.

Medical images (e.g., captured via the X-ray source 304 and an X-ray detector of the portable DR machine 300), visible light images (e.g., captured utilizing the camera system 306), and/or recorded audio (e.g., captured utilizing microphone(s) 216) acquired pursuant to a medical imaging session for a particular patient may be stored in association with the identity of the particular patient. For example, FIG. 2 shows that the radiography system(s) 222, the MRI system(s) 224, the ultrasound system(s) 226, and/or the other system(s) 228 may be in communication with a network 230. The network may comprise one or more links that enable the transport of information between and/or among systems, modules, and/or devices. FIG. 2 also illustrates server(s) 232 in communication with the network 230 and therefore in communication with the radiography system(s) 222, the MRI system(s) 224, the ultrasound system(s) 226, and/or the other system(s) 228. The server(s) 232 may comprise any of the components discussed hereinabove with reference to FIG. 2, such as processor(s) 202, storage 204, I/O system(s) 218, communication system(s) 220, etc.

The server(s) 232 may be configured to receive and store information from the radiography system(s) 222, the MRI system(s) 224, the ultrasound system(s) 226, and/or the other system(s) 228 in association with particular patients. The server(s) 232 may thus operate similar to a patient database and/or a picture archiving and communication system (PACS). For example, a radiography system 222 (e.g., portable DR machine 300) may be utilized to capture one or more X-ray images, visible light images, and/or audio recordings of a human patient named "Einstein, Albert" pursuant to a medical imaging session for "Einstein, Albert". The server(s) 232 may receive and store the medical images, visible light images, and/or recorded audio (e.g., over the network 230 via communication system(s) 220) in association with the identity of "Einstein, Albert" such that the information becomes accessible to make diagnostic, treatment, and/or other decisions for "Einstein, Albert" (one will appreciate that other patient identifiers in addition to patient name may be used, such as birthday, medical record number, etc.). For instance, "Einstein, Albert" may receive a medical treatment over time, and medical images may be captured for "Einstein, Albert" over several timepoints to assess effectiveness of the medical treatment. Such assessment over time would rely on proper association of medical images for "Einstein, Albert" with the identity of "Einstein, Albert" within the server(s) 232. As will be described in more detail hereinbelow, the storage of visible light images and/or patient audio, in addition to medical images, in association with patient identity may contribute to facilitating avoidance of errors in medical imaging (e.g., wrong-patient errors).

Figure 4B:
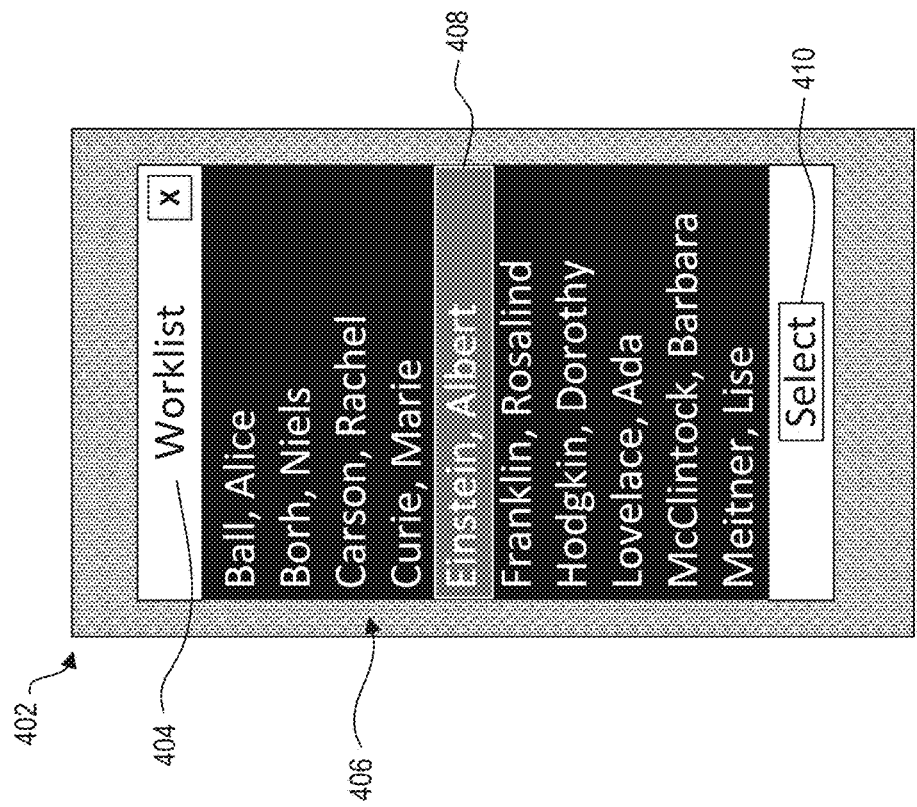
FIG. 4B, FIG. 4C, and FIG. 4D illustrate example displayable content for facilitating prevention of wrong-patient errors based upon previously captured imagery.
Figure 4A:
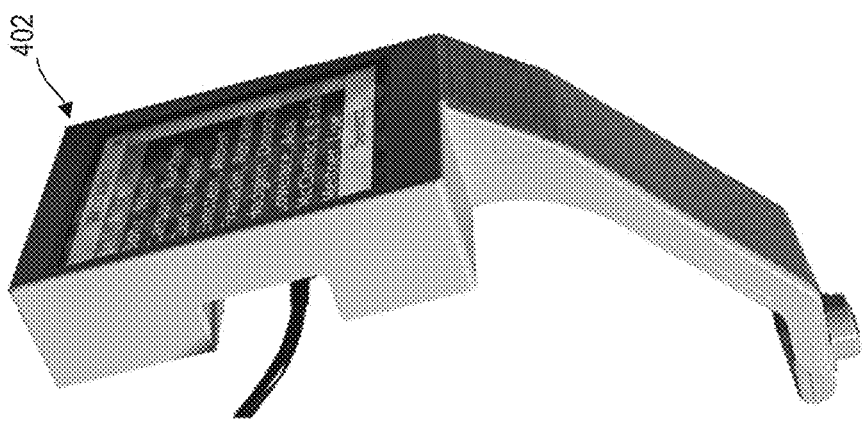
FIG. 4A illustrates an example user interface of a medical imaging system.

FIG. 4A illustrates an example user interface 402. The user interface 402 comprises an I/O system 218 of a medical imaging system (e.g., radiography system(s) 222, the MM system(s) 224, the ultrasound system(s) 226, and/or the other system(s) 228). The user interface 402 may be one of multiple user interfaces associated with the medical imaging system. For example, the user interface 402 may be associated with control of visible light sensor(s) 212 and/or microphone(s) 216 of the medical imaging system, whereas the medical imaging system may comprise one or more other user interfaces associated with control of medical imaging sensor(s) 214. Alternatively, the user interface 402 may be associated with control of the medical imaging sensor(s) 214 and may be separate from one or more other user interfaces of the medical imaging system for facilitating control of the visible light sensor(s) 212 and/or microphone(s) 216 of the medical imaging system. As yet another alternative, the user interface 402 may comprise a combined user interface that controls the visible light sensor(s) 212, the medical imaging sensor(s) 214, and/or the microphone(s) 216.

Although the user interface 402 of FIG. 4A is illustrated as a touch screen interface, other types of user interfaces (e.g., I/O system(s) 218) are within the scope of the present disclosure.

Figure 4D:
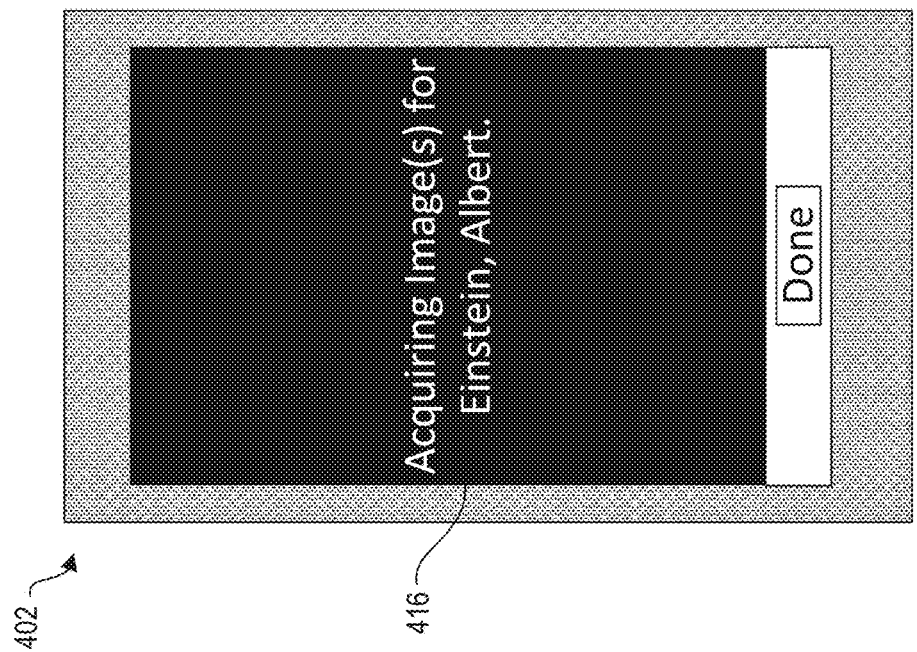
Figure 4C:
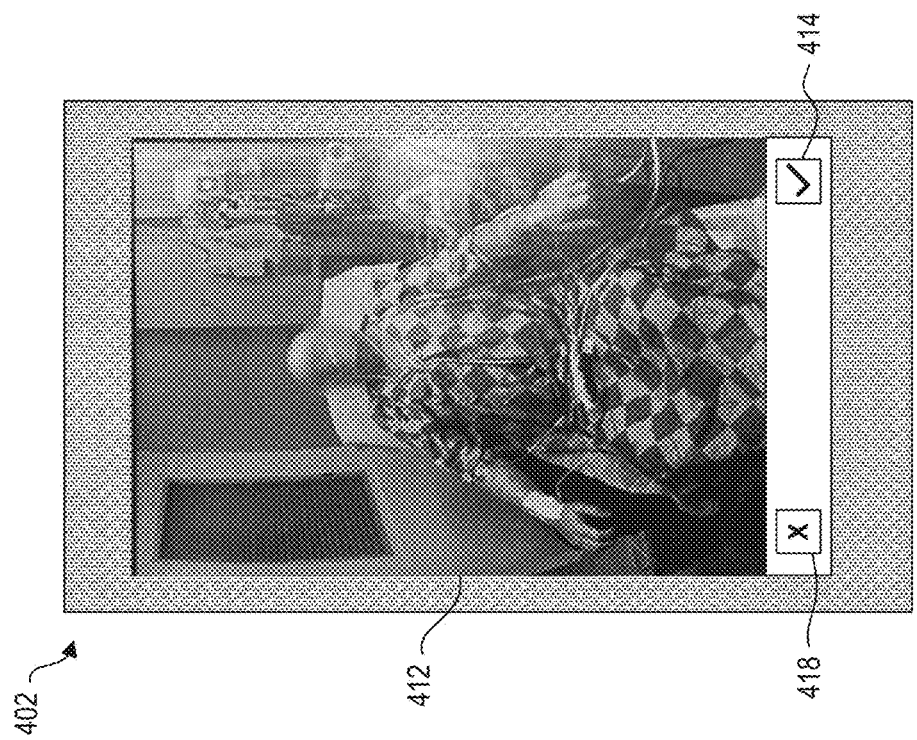

FIG. 4B, FIG. 4C, and FIG. 4D illustrate example displayable content for facilitating prevention of wrong-patient errors based upon previously captured imagery. The discussion of FIGS. 4B, 4C, and 4D will follow from the example given above of an imaging session previously performed for "Einstein, Albert". One will appreciate, in view of the present disclosure, that the particular examples given in reference to the Figures are provided by way of illustration and explanation only, and are not limiting of the principles disclosed herein.

Continuing with this example, based upon the previous imaging session for "Einstein, Albert", one or more medical images (e.g., captured via the X-ray source 304 and X-ray sensors of the portable DR machine 300) and one or more visible light images (e.g., captured via the camera system 306 of the portable DR machine 300) were stored in association with the identity of "Einstein, Albert" (e.g., within the server(s) 232). The discussion of FIGS. 4B, 4C, and 4D illustrates example acts that may be performed to facilitate capturing and storage of additional, updated, or current medical images of "Einstein, Albert" in a manner that avoids wrong-patient errors (e.g., capturing images of a human subject who is different from "Einstein, Albert" and storing such images in association with the identity of "Einstein, Albert" within the patient database).

FIG. 4B illustrates the user interface 402 of FIG. 4A and shows a patient worklist 404 that displays a plurality of patient names 406. The user interface 402 may be operated by a medical imaging technologist (or any other user) tasked with acquiring additional medical images of "Einstein, Albert". The user interface 402 may thus receive a selection 408 of a current imaging subject (in this case, "Einstein, Albert", a medical patient) for whom a current or updated medical imaging study is to be performed. The current medical imaging study may include capturing current or updated medical images of the current imaging subject using a medical image sensor system (e.g., a first image sensor system of a first imaging modality). The medical image sensor system may comprise medical imaging sensor(s) 214 of radiography system(s) 222, the MRI system(s) 224, the ultrasound system(s) 226, and/or the other system(s) 228.

Although the example of FIG. 4B illustrates receiving the selection 408 via user input provided at the user interface 402, the selection 408 may be received by a system in other ways. For instance, the selection may be received by voice commands of the imaging subject or a technologist (or other person) tasked with performing the imaging session. For example, the technologist may dictate the name of the patient for whom the current imaging study is intended, and the system may perform speech recognition to determine a name (and/or other patient identifying information) dictated by the technologist to receive the selection based on the name (and/or other patient identifying information) determined by speech recognition.

The example of FIG. 4B illustrates a "select" button 410 whereby a technologist (or other person) tasked with performing the imaging session may confirm the selection 408 of the current imaging subject patient for whom the current imaging study is intended (in this case, "Einstein, Albert"). Responsive to receiving and/or confirmation of the selection 408 of the current imaging subject for whom the current imaging study is intended, a system may access (or obtain, retrieve, receive, etc.) a set of one or more previous images stored within the server(s) 232 (and/or any other data repository of patients/imaging subjects) in association with the patient identity indicated by the selection 408 (in this case, "Einstein, Albert"). The one or more previous images were captured at a previous timepoint (e.g., during a previous imaging study) and depict a previous imaging subject associated with the identity "Einstein, Albert" (i.e., the intended subject of the current imaging study). The one or more previous images may depict the previous imaging subject according to an imaging modality that is different than the medical imaging modality intended for use to capture medical images during the current imaging study. For instance, the one or more previous images may comprise visible light images (e.g., captured utilizing visible light sensor(s) 212), whereas the medical imaging modality for the current imaging study may comprise radiographs, MRI images, ultrasound images, etc. (e.g., captured utilizing medical imaging sensor(s) 214).

FIG. 4C illustrates an example previous image 412 displayed on the user interface 402. As indicated above, the previous image 412 comprises a visible light image of a previously captured patient that was stored within the server(s) 232 in association with the patient identified as "Einstein, Albert". By displaying the previous image 412 on the user interface 402, a technologist may assess the patient features shown in the previous image 412 for comparison with features of the current patient queued for the current medical imaging study to determine whether the current patient matches the previously captured patient as represented in the previous image 412.

If the technologist determines that the patients are the same (e.g., using the previous image 412), the technologist may proceed with the current imaging study of the current patient, such as by providing further user input at the user interface 402 (e.g., via selectable element 414) to confirm that the identity of the current (e.g., physically present) patient queued for the current imaging study (putatively "Einstein, Albert") matches the previous patient as depicted in the previous image 412 (also putatively "Einstein, Albert"). FIG. 4D illustrates example content 416 that may be displayed on the user interface 402 in response to receiving a confirmation that the current patient matches the previous patient (e.g., responsive to user input directed to the selectable element 414).

In some instances, the medical imaging sensor associated with the user interface 402 is functionally prevented and/or disabled from capturing medical images for the current imaging study unless user input confirming that the previous patient matches the current patient is received. Such functionality may protect patients from being wrongly exposed to medical imaging radiation and/or other side effects of medical imaging, and may contribute to prevention of downstream errors that can result from wrong-patient errors.

Proceeding with the current imaging study may include capturing medical images of the current patient utilizing a medical imaging system (e.g., medical imaging sensor(s) 214 for capturing images of the first imaging modality). The newly captured medical images may be stored in association with the selected patient identity (e.g., "Einstein, Albert") within a patient data repository.

Alternatively, if the technologist determines that the identity of the current patient does not match the identity of previously imaged patient as indicated by the previous image 412, the technologist may refrain or be prevented from proceeding with the current imaging study. For example, the technologist may provide user input indicating that the previous patient and the current patient do not match (e.g., via selectable element 418). Thus, by presenting previous patient photographs at the point of current/updated imaging as described above, capturing medical images of incorrect or unintended patients may be avoided, and downstream errors that may result from incorrectly associating wrong-patient images with patients within a patient database may be avoided.

In some instances, the current imaging study further includes capturing additional visible light images of the current patient (e.g., utilizing visible light sensor(s) 212 to capture images of the second imaging modality). The newly captured visible light images of the current patient may additionally be stored in association with the selected patient identity (e.g., "Einstein, Albert") within a patient database. The additional visible light images of the current patient may be accessed later to verify that the identity of a future patient for a future imaging study matches the identity of the current patient (e.g., to further prevent future potential wrong-patient errors).

One will appreciate, in view of the present disclosure, that the particulars of the example shown and described with reference to FIGS. 4A through 4D are provided by way of explanation only, and are not necessarily limiting of the principles disclosed herein. For instance, different user interfaces and/or display systems than the user interface 402 of FIGS. 4A through 4D may be utilized in accordance with the present disclosure. For example, a previous image of a patient may be pushed or otherwise transmitted to a display device that is untethered from a medical imaging system for display thereon (e.g., a smartphone, tablet, workstation, etc.).

Although the foregoing example focuses on display of a previous visible light image of a previous patient associated with a selected identity of a current patient for a current imaging study, other previously captured content may be presented and/or utilized in accordance with the present disclosure. For instance, previous medical imagery of the previous patient may be displayed in addition to or in combination with the visible light imagery of the previous patient. Furthermore, it should be noted that multiple previous images may be displayed, such as multiple previous image frames that form video frames of a previously captured video of the previous patient (previously captured audio may accompany the previously captured video).

As will be described in more detail hereinbelow, previously captured patient audio may be utilized to facilitate prevention of wrong-patient errors.

Figure 5B:
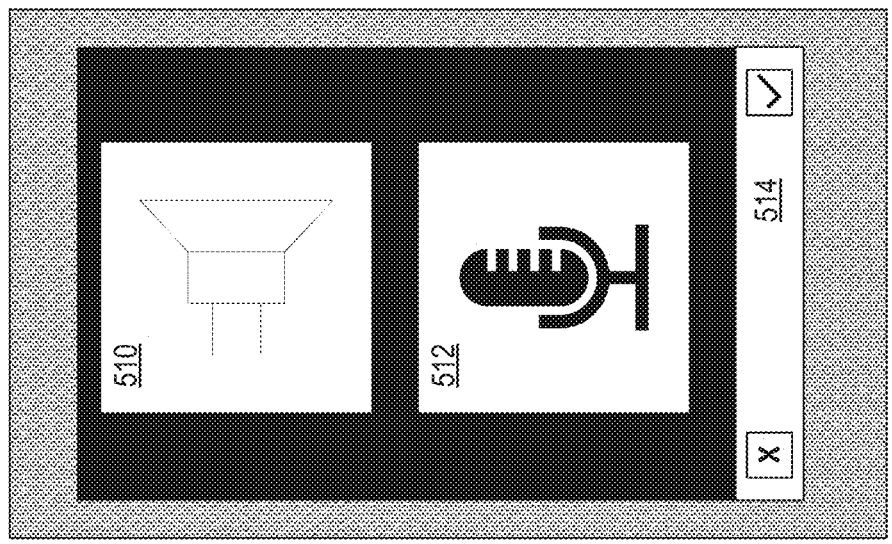
FIG. 5A and FIG. 5B illustrate example displayable content in association with acts for facilitating prevention of wrong-patient errors based upon previously captured audio.
Figure 5A:
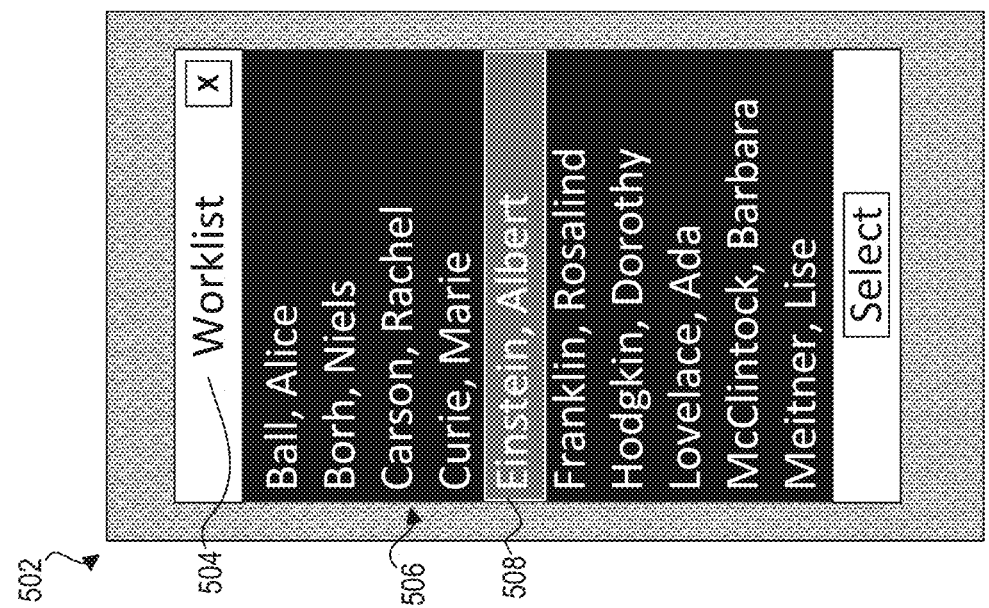

FIG. 5A and FIG. 5B illustrate example displayable content in association with acts for facilitating prevention of wrong-patient errors based upon previously captured audio. Similar to the discussion of FIGS. 4B, 4C, and 4D, the discussion of FIGS. 5A and 5B follows from the example given above of an imaging session previously performed for "Einstein, Albert". Based upon the previous imaging session for "Einstein, Albert", one or more medical images (e.g., captured via the X-ray source 304 and X-ray sensors of the portable DR machine 300) and one or more audio recordings (e.g., captured via microphone(s) 216 associated with a medical imaging system) were stored in association with the identity of "Einstein, Albert" (e.g., within the server(s) 232). The discussion of FIGS. 5A and 5B illustrates example acts that may be performed utilizing the previously stored patient audio to facilitate capturing and storage of additional, updated, or current medical images of "Einstein, Albert" in a manner that avoids wrong-patient errors.

FIG. 5A illustrates a user interface 502 that corresponds to the user interface 402 of FIG. 4B. The user interface 502 also includes a patient worklist 504 that displays a plurality of patient names 506, with a selection 508 of a current imaging subject ("Einstein, Albert", a medical patient) for whom a current or updated medical imaging study is intended to be performed (other modes of selecting the current imaging subject are within the scope of the present disclosure). As before, the current medical imaging study may include capturing current or updated medical images of the current imaging subject using a medical image sensor system (e.g., a first image sensor system of a first imaging modality), and the medical image sensor system may comprise medical imaging sensor(s) 214 of radiography system(s) 222, the MRI system(s) 224, the ultrasound system(s) 226, and/or the other system(s) 228.

Responsive to receiving and/or confirmation of the selection 508 of the current imaging subject for whom the current imaging study is intended, a system may perform various actions based upon the previously recorded patient audio associated with "Einstein, Albert" to facilitate prevention of wrong-patient errors. For example, FIG. 5B illustrates an audio playback icon 510 and an audio recording icon 512 displayed on the user interface 502. Selection of the audio playback icon 510 may trigger accessing and/or playback the previously stored patient audio associated with the selected current imaging subject ("Einstein, Albert"). The previously stored patient audio includes vocalizations of the previous imaging subject as captured at the time of the previous imaging study noted above. The previously stored audio may be played back on a speaker (e.g., I/O system 218) associated with a medical imaging device and/or other device (e.g., a smartphone, tablet, workstation, etc.).

By presenting the previously stored patient audio recording(s) prior to performance of the current imaging study, a technologist may assess the vocal attributes of the previous imaging subject as represented in the previously stored patient audio for comparison with vocal attributes of the current patient queued for the current medical imaging study to determine whether the current patient matches the previously captured patient as represented by the previously stored patient audio recording(s). For instance, the previously stored patient audio may record the previous imaging subject stating their name and birthday, and the current imaging subject may similarly be prompted to state their name and birthday (and/or other similar speech content) for ease of comparison of vocal attributes.

If the technologist determines that the previous patient and the current patient match, the technologist may proceed with the current imaging study of the current patient, such as by providing further user input at the user interface 502 (e.g., via selectable element 514) to confirm that the identity of the current (e.g., physically present) patient queued for the current imaging study (putatively "Einstein, Albert") matches the previous patient as represented by the previous audio recording(s). As before, the medical imaging sensor may be functionally prevented and/or disabled from capturing medical images for the current imaging study unless user input confirming that the previous patient matches the current patient is received. Alternatively, if the technologist determines that the identity of the current patient does not match the identity of previously imaged patient as indicated by the previous patient audio recording(s), the technologist may refrain or be prevented from proceeding with the current imaging study.

Additionally, or alternatively, selection of the audio recording icon 512 may trigger capturing of a current audio recording of the current imaging subject. For example, the current imaging subject may be prompted to state a certain key phrase or dictate identifying information (e.g., the patient's name, the patient's birthday, etc.). The current audio recording of the current imaging subject may be utilized in a voice authentication operation to determine whether the current imaging subject matches the previous imaging subject. For example, the previous audio recording(s) associated with the identity of the selected patient (e.g., "Einstein, Albert") may be used to generate a voice signature or voiceprint for the selected patient. The voice signature or voiceprint may comprise a mathematical model (e.g., a universal background model, a composite model such as a DNN model, and/or others) of vocal characteristics generated using the previous audio recording (s) associated with the selected (previously imaged) patient. The voice signature or voiceprint may be generated utilizing various techniques, such as feature extraction approaches, deep learning approaches, etc.

The current audio recording of the current imaging subject (e.g., captured responsive to selection of the audio recording icon 512) may be evaluated utilizing the voice signature or voiceprint to determine whether the identity of the current imaging subject who provided the vocalization(s) for the current audio recording(s) matches the previous imaging subject who provided the vocalization(s) for the previous audio recording(s) (e.g., via a voice authentication process or verification/scoring process).

If the voice authentication indicates a match between the current patient and the previous patient, a system may enable the current imaging session to proceed (e.g., by unlocking medical imaging functionality of the medical imaging system). If the voice authentication indicates a mismatch between the current patient and the previous patient, the system may refrain from enabling the current imaging session to proceed (e.g., by locking or maintaining disablement of medical imaging functionality of the medical imaging system, or by providing a notification on a user interface).

Although the discussion of FIG. 5B provides an example in which the previous audio recording playback functions and the current audio recording functions are triggered by selection of user interface elements (icons 510 and 512, respectively), such functions may be triggered in response to other triggering events (e.g., receiving of the selection 508, which selection may take on forms that are different than the user interface selection 508 shown in FIG. 5A). Furthermore, in some implementations, a system is configured to facilitate only one of audio playback or voice authentication as a means for preventing wrong-patient errors, whereas, in some implementations, a system provides both audio playback and voice authentication functionality as means for preventing wrong-patient errors. In some instances, a combination of previous image/video presentation (e.g., see FIGS. 4A through 4D and attendant description), audio playback, and/or voice authentication is implemented on a medical imaging system to prevent wrong-patient errors in medical imaging.

Figure 6:
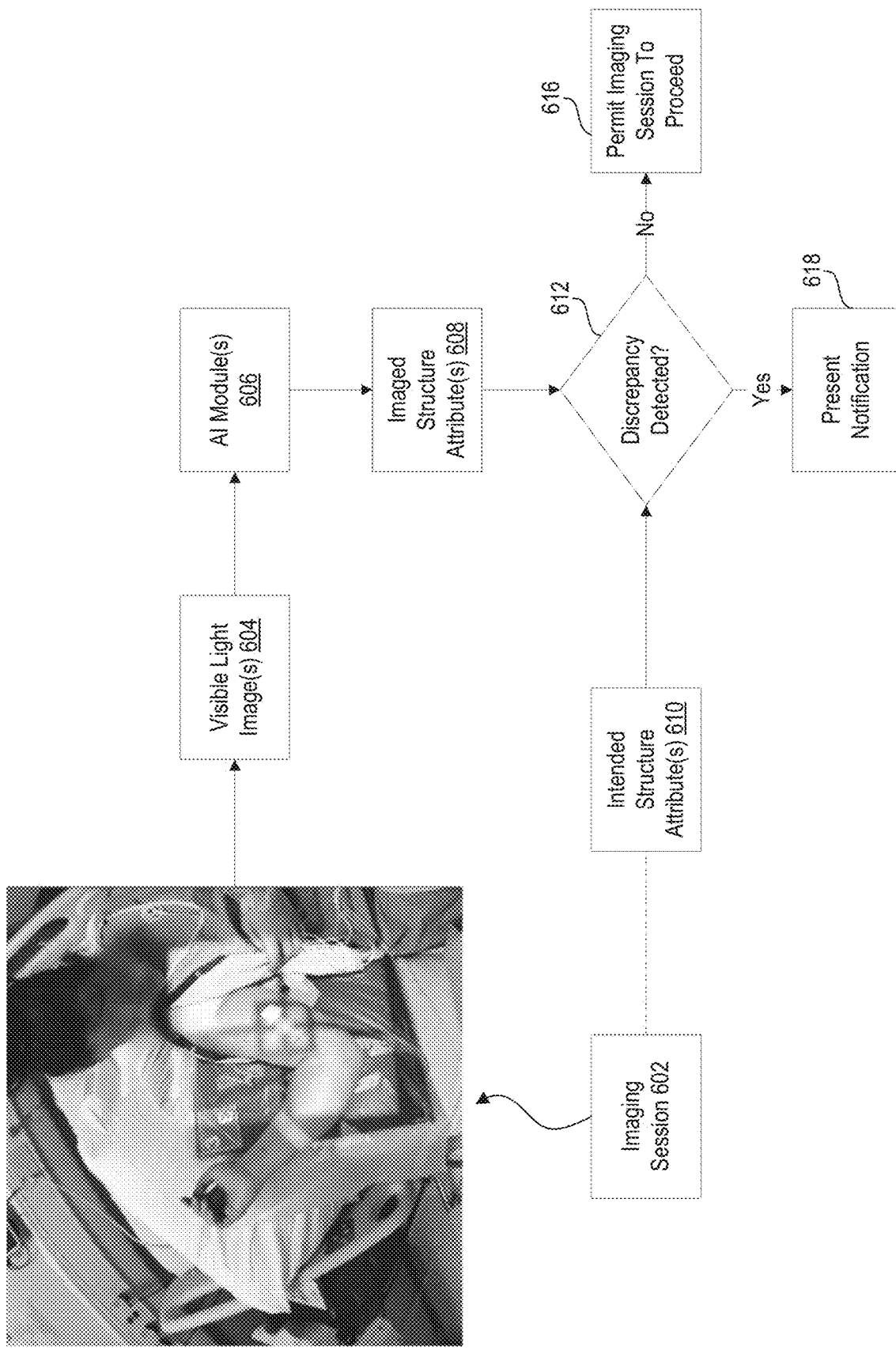
FIG. 6 illustrates a conceptual representation of preventing laterality errors.

FIG. 6 illustrates a conceptual representation of preventing laterality errors. In particular, FIG. 6 illustrates an example representation of preparation for an imaging session 602, in which an arm of a patient is targeted for medical imaging (e.g., utilizing a portable DR machine 300). Although an arm of a human patient is the target of the imaging session 602, any type of structure (e.g., another bodily structure of a human patient, or non-human imaging subject) may be the target of an imaging session in accordance with the present disclosure.

In the depiction of preparation for the imaging session 602 in FIG. 6, no medical imagery has yet been captured of the patient's arm pursuant to the imaging session 602. The patient's arm is only targeted for medical imaging (as indicated by the illuminated crosshairs). The patient's arm may be targeted in accordance with predefined intended structure attribute(s) 610, which may indicate particular bodily structure attributes that are intended to be embodied by the bodily structure that becomes imaged during the imaging session 602. For instance, structure attribute(s) 610 may define the intended bodily structure (e.g., arm, leg, chest, portions thereof, etc.) for which medical imaging is desired/needed, and/or the intended laterality of the specific bodily structure (e.g., left, right). For example, the intended structure attribute(s) 610 may be based upon a physician's order for X-ray imaging of the patient's right humerus. A technologist may then utilize the intended structure attribute(s) 610 to arrange the medical imaging system (e.g., a portable DR machine 300) to capture the portion of the patient's body specified by the intended structure attribute(s) 610.

Laterality errors sometimes arise, however, when a technologist incorrectly interprets or incorrectly carries out intended structure attribute(s) 610 for a medical imaging session. For example, where the intended structure attribute(s) 610 indicate that imaging is to be performed on a patient's right humerus, a technologist may inadvertently target the patient's left humerus for medical imaging, which may result in a laterality error and other downstream consequences.

To prevent such laterality errors, a visible light sensor 212 (e.g., a camera system 306 of a portable DR machine 300) may be utilized to capture visible light image(s) 604 of the patient bodily structure that is currently targeted by the medical imaging sensor (e.g., the X-ray head 302 of the portable DR machine 300) for the imaging session 602. In the example of FIG. 6, the visible light image(s) 604 may capture the right arm of the patient. The visible light image(s) 604 comprise a different imaging modality than the medical imaging modality associated with the imaging session 602 (e.g., X-ray). The visible light image(s) 604 are captured prior to any medical images for the imaging session 602 and may therefore be regarded as "initial images".

FIG. 6 illustrates that the visible light image(s) 604 (or at least a portion thereof) may be utilized as input to artificial intelligence module(s) 606 (AI module(s) 606). The AI module(s) 606 are configured/trained to output attributes of structures represented in the visible light image(s) 604 (e.g., imaged structure attribute(s) 608) based upon input imagery/image data. Such imaged structure attribute(s) 608 may comprise the laterality of imaged structures (e.g., "imaged laterality") and/or structure type for imaged structures. The AI module(s) 606 may be trained utilizing training data comprising images of bodily structures (and/or other environmental markers/structures that may be implemented in medical imaging sessions) that are associated with labels/tags indicating laterality and/or structure type. The AI module(s) 606 may comprise any type of artificial intelligence architecture, such as one or more convolutional neural networks.

In the example of FIG. 6, the imaged structure attribute(s) 608 as determined via the AI module(s) 606 may indicate an imaged laterality of "right". The imaged structure attribute(s) 608 may be compared to the intended structure attribute(s) 610 to determine whether a discrepancy exists, in accordance with decision block 612 of FIG. 6. When no discrepancy is detected between the imaged structure attribute(s) 608 and the intended structure attribute(s) 610 (e.g., the imaged structure attribute(s) 608 indicates an imaged laterality of "right" and the intended structure attribute(s) 610 indicates an intended laterality of "right"), the imaging session 602 may be permitted to proceed, in accordance with act 616 of FIG. 6 (e.g., medical imaging acquisition functionality for the medical imaging system may be conditioned on detecting no discrepancy between the intended structure attribute(s) 610 and the imaged structure attribute(s) 608, and/or a notification may be presented indicating that a technologist may proceed with the medical imaging session 602).

In contrast, when a discrepancy is detected between the imaged structure attributes 608 and the intended structure attribute(s) 610 (e.g., the imaged structure attribute(s) 608 indicates an imaged laterality of "right" and the intended structure attribute(s) 610 indicates an intended laterality of "left"), a notification may be presented, in accordance with act 618 of FIG. 6. The notification may take on various forms, such as an audible alert and/or a visual alert provided on a user interface associated with the medical imaging system to prevent the technologist from proceeding with the imaging session 602. Additionally, or alternatively, the medical imaging system may enter or remain in a locked state preventing the imaging session 602 from proceeding when a discrepancy is detected between the imaged structure attribute(s) 608 and the intended structure attribute(s) 610. Such functionality may thus prevent wrong-patient errors from being recorded in patient medical image databases.

In some instances, a system may present the input and/or output of the AI module(s) 606 (e.g., the visible light image(s) 604 and/or the imaged structure attribute(s) 608) to allow a human user (e.g., the technologist) to indicate (e.g., via user input) whether the imaged structure attribute label(s) generated by the AI module(s) 606 are erroneous, thereby facilitating further training and/or fine-tuning of the AI module(s) 606.

As noted above, the intended structure attribute(s) 610 and/or the imaged structure attribute(s) 608 may additionally or alternatively indicate the intended structure type and/or the imaged structure type, respectively. Thus, in some instances, the AI module(s) 606 may additionally or alternatively be configured to determine structure type based upon image data input (e.g., visible light image(s) 604 of the targeted structure for imaging during the imaging session 602). Discrepancies between intended structure type (as indicated by the intended structure attribute(s) 610) and imaged structure type (as indicated by the imaged structure attribute(s) 608) may thus be detected and handled in accordance with decision block 612 and acts 616 and 618 of FIG. 6.

Example Method(s) for Preventing Errors in Medical Imaging

The following discussion now refers to a number of methods (e.g., computer-implementable or system-implementable methods) and/or method acts that may be performed in accordance with the present disclosure. Although the method acts are discussed in a certain order and illustrated in a flow chart as occurring in a particular order, no particular ordering is required unless specifically stated, or required because an act is dependent on another act being completed prior to the act being performed. One will appreciate that certain embodiments of the present disclosure may omit one or more of the acts described herein.

Figure 9:
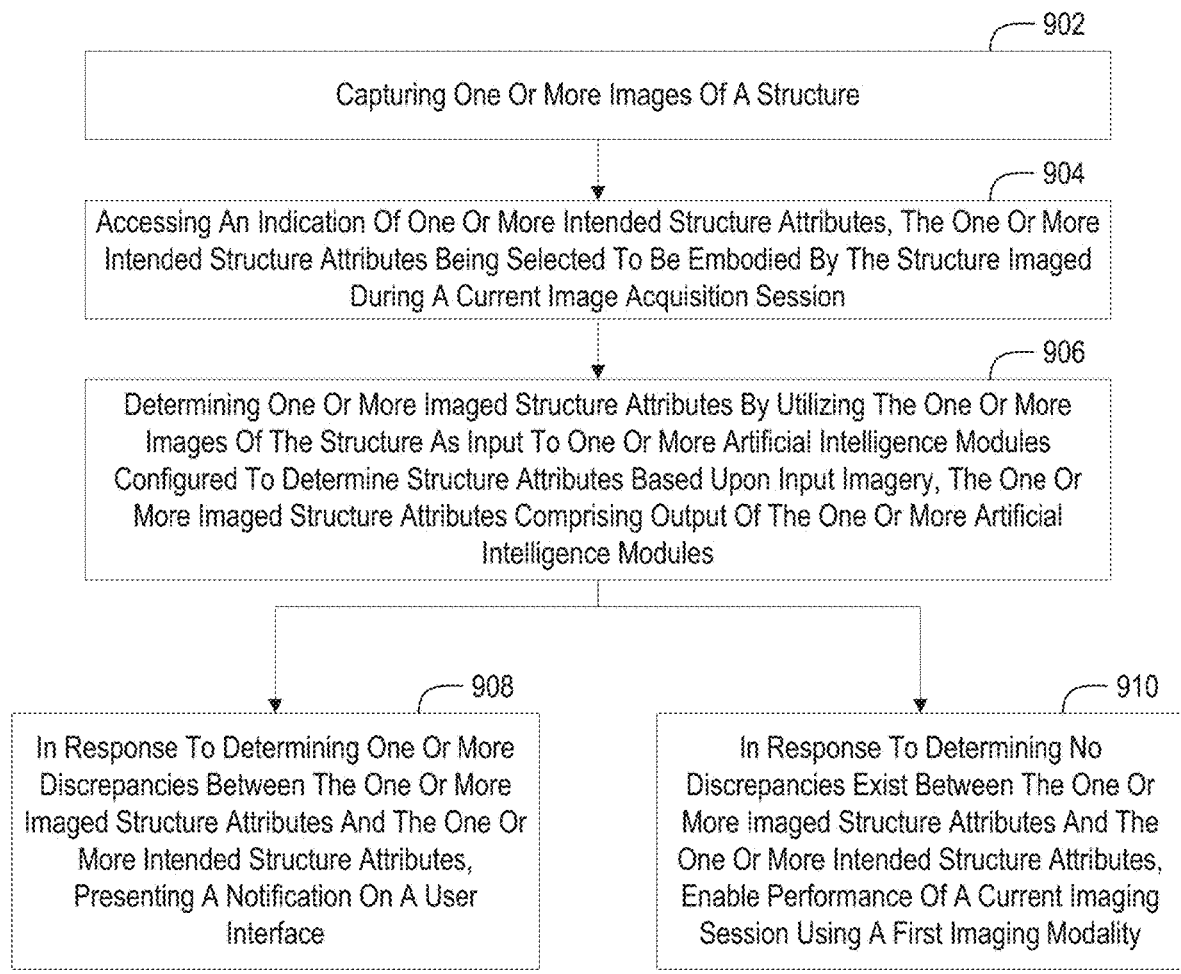

FIG. 7, FIG. 8, and FIG. 9 illustrate example flow diagrams 700, 800, and 900, respectively, depicting acts associated with preventing errors in medical imaging.

Act 702 of flow diagram 700 of FIG. 7 includes receiving a selection of a current imaging subject, the current imaging subject being selected for a current image acquisition session comprising capturing one or more current images of the current imaging subject utilizing at least a first image sensor system of a first imaging modality. In some instances, act 702 is performed utilizing processor(s) 202, storage 204, sensor(s) 210, I/O system(s) 218, communication system(s) 220, and/or other components of radiography system(s) 222, MRI system(s) 224, ultrasound system(s) 226, server(s) 232, and/or other system(s) 228.

In some instances, receiving the selection of the current imaging subject comprises receiving user input selecting the current imaging subject. The first imaging modality may comprise a medical imaging modality. The current imaging subject may comprise a medical patient.

Act 704 of flow diagram 700 includes accessing a set of one or more previous images of a previous imaging subject, the one or more previous images depicting the previous imaging subject according to at least a second imaging modality that is different from the first imaging modality. In some instances, act 704 is performed utilizing processor(s) 202, storage 204, sensor(s) 210, I/O system(s) 218, communication system(s) 220, and/or other components of radiography system(s) 222, MRI system(s) 224, ultrasound system(s) 226, server(s) 232, and/or other system(s) 228.

The one or more previous images of the previous imaging subject are associated with one or more image capture timepoints that temporally precede the current image acquisition session. In some implementations, the second imaging modality comprises a visible spectrum imaging modality. In some instances, accessing the set of one or more previous images of the previous imaging subject comprises accessing a data repository of imaging subjects based upon the selection of the current imaging subject. The one or more previous images may comprise one or more video frames. In some instances, the set of one or more previous images of the previous subject further comprises at least one previous image depicting the previous subject according to the first imaging modality.

Act 706 of flow diagram 700 includes presenting the one or more previous images on a display system. In some instances, act 706 is performed utilizing processor(s) 202, storage 204, sensor(s) 210, I/O system(s) 218, communication system(s) 220, and/or other components of radiography system(s) 222, MRI system(s) 224, ultrasound system(s) 226, server(s) 232, and/or other system(s) 228. In some instances, the display system comprises a user interface of the first image sensor system of the first imaging modality.

Act 708 of flow diagram 700 includes, in response to determining that the previous imaging subject matches the current imaging subject based upon the one or more previous images of the second imaging modality, performing the current image acquisition session by capturing the one or more current images of the current imaging subject utilizing at least the first image sensor system of the first imaging modality. In some instances, act 708 is performed utilizing processor(s) 202, storage 204, sensor(s) 210, I/O system(s) 218, communication system(s) 220, and/or other components of radiography system(s) 222, MRI system(s) 224, ultrasound system(s) 226, server(s) 232, and/or other system(s) 228.

In some implementations, the first image sensor system is configured to be prevented from acquiring the one or more current images of the current imaging subject unless the previous imaging subject matches the current imaging subject. In some instances, determining that the previous imaging subject matches the current imaging subject based upon the one or more previous images of the second imaging modality comprises receiving user input indicating that the previous imaging subject matches the current imaging subject. Determining that the previous imaging subject matches the current imaging subject may be further based upon one or more audio recordings of the current imaging subject. In some instances, the one or more current images or the one or more previous images comprise one or more video frames. The current image acquisition session may further comprise capturing one or more additional current images of the current imaging subject utilizing at least a second image sensor system of the second imaging modality (e.g., in the form of single image frame(s) or video frames (which may include accompanying audio)). The current image acquisition session may further comprise capturing patient audio (e.g., to generate or update a voiceprint or voice signature). Furthermore, in some implementations, the display system of act 706 comprises a user interface of the second image sensor system of the second imaging modality.

Act 710 of flow diagram 700 includes associating the one or more current images with the previous imaging subject within a subject data repository. In some instances, act 710 is performed utilizing processor(s) 202, storage 204, sensor(s) 210, I/O system(s) 218, communication system(s) 220, and/or other components of radiography system(s) 222, MM system(s) 224, ultrasound system(s) 226, server(s) 232, and/or other system(s) 228.

Act 802 of flow diagram 800 of FIG. 8 includes receiving a selection of a current imaging subject, the current imaging subject being selected for a current image acquisition session comprising capturing one or more current images of the current imaging subject utilizing at least a first image sensor system of a first imaging modality. In some instances, act 802 is performed utilizing processor(s) 202, storage 204, sensor(s) 210, I/O system(s) 218, communication system(s) 220, and/or other components of radiography system(s) 222, MRI system(s) 224, ultrasound system(s) 226, server(s) 232, and/or other system(s) 228.

Act 804 of flow diagram 800 includes accessing one or more previous audio recordings or one or more voice signatures of a previous imaging subject. In some instances, act 804 is performed utilizing processor(s) 202, storage 204, sensor(s) 210, I/O system(s) 218, communication system(s) 220, and/or other components of radiography system(s) 222, MM system(s) 224, ultrasound system(s) 226, server(s) 232, and/or other system(s) 228. The one or more previous audio recordings may capture vocalization of the previous imaging subject at one or more audio recording timepoints that temporally precede the current image acquisition session. The one or more voice signatures may comprise one or more models generated using a set of previous audio recordings capturing vocalization of the previous imaging subject.

Act 806 of flow diagram 800 includes, in response to determining that the previous imaging subject matches the current imaging subject based upon the one or more previous audio recordings or the one or more voice signatures, performing the current image acquisition session by capturing the one or more current images of the current imaging subject utilizing at least the first image sensor system of the first imaging modality. In some instances, act 806 is performed utilizing processor(s) 202, storage 204, sensor(s) 210, I/O system(s) 218, communication system(s) 220, and/or other components of radiography system(s) 222, MRI system(s) 224, ultrasound system(s) 226, server(s) 232, and/or other system(s) 228.

In some implementations, determining that the previous imaging subject matches the current imaging subject based upon the one or more previous audio recordings or the one or more voice signatures comprises (i) presenting the one or more previous audio recordings on an audio playback system and (ii) receiving user input indicating that the previous imaging subject matches the current imaging subject.

In some implementations, determining that the previous imaging subject matches the current imaging subject based upon the one or more previous audio recordings or the one or more voice signatures comprises (i) obtaining a current audio recording of the current imaging subject and (ii) performing voice authentication using the current audio recording and the one or more voice signatures to determine whether the previous imaging subject matches the current imaging subject.

Act 902 of flow diagram 900 of FIG. 9 includes capturing one or more images of a structure. In some instances, act 902 is performed utilizing processor(s) 202, storage 204, sensor(s) 210, I/O system(s) 218, communication system(s) 220, and/or other components of radiography system(s) 222, MRI system(s) 224, ultrasound system(s) 226, server(s) 232, and/or other system(s) 228.

Act 904 of flow diagram 900 includes accessing an indication of one or more intended structure attributes, the one or more intended structure attributes being selected to be embodied by the structure imaged during a current image acquisition session. In some instances, act 904 is performed utilizing processor(s) 202, storage 204, sensor(s) 210, I/O system(s) 218, communication system(s) 220, and/or other components of radiography system(s) 222, MM system(s) 224, ultrasound system(s) 226, server(s) 232, and/or other system(s) 228. In some implementations, the one or more intended structure attributes comprise an intended laterality.

Act 906 of flow diagram 900 includes determining one or more imaged structure attributes by utilizing the one or more images of the structure as input to one or more artificial intelligence modules configured to determine structure attributes based upon input imagery, the one or more imaged structure attributes comprising output of the one or more artificial intelligence modules. In some instances, act 906 is performed utilizing processor(s) 202, storage 204, sensor(s) 210, I/O system(s) 218, communication system(s) 220, and/or other components of radiography system(s) 222, MRI system(s) 224, ultrasound system(s) 226, server(s) 232, and/or other system(s) 228. In some instances, the one or more imaged structure attributes comprise an imaged laterality. The one or more artificial intelligence modules may comprise one or more convolutional neural networks.

Act 908 of flow diagram 900 includes, in response to determining one or more discrepancies between the one or more imaged structure attributes and the one or more intended structure attributes, presenting a notification on a user interface. In some instances, act 908 is performed utilizing processor(s) 202, storage 204, sensor(s) 210, I/O system(s) 218, communication system(s) 220, and/or other components of radiography system(s) 222, MM system(s) 224, ultrasound system(s) 226, server(s) 232, and/or other system(s) 228. The notification may be configured to prevent performance of a current imaging session using a first imaging modality. The first imaging modality may comprise a medical imaging modality. The first imaging modality may be different than a second imaging modality associated with the one or more images captured in accordance with act 902.

Act 910 of flow diagram 900 includes, in response to determining no discrepancies exist between the one or more imaged structure attributes and the one or more intended structure attributes, enable performance of a current imaging session using a first imaging. In some instances, act 910 is performed utilizing processor(s) 202, storage 204, sensor(s) 210, I/O system(s) 218, communication system(s) 220, and/or other components of radiography system(s) 222, MRI system(s) 224, ultrasound system(s) 226, server(s) 232, and/or other system(s) 228. In some implementations, the first imaging modality comprises a medical imaging modality. The first imaging modality may be different than a second imaging modality associated with the one or more images captured in accordance with act 902.

Abbreviated List of Defined Terms

To assist in understanding the scope and content of the foregoing and forthcoming written description and appended claims, a select few terms are defined directly below.

The terms "physician", "clinician", "radiologist", and "technologist" as used herein generally refer to any licensed and/or trained person prescribing, administering, or overseeing the diagnosis and/or treatment of a patient or who otherwise tends to the wellness of a patient. This term may, when contextually appropriate, include any licensed medical professional, such as a physician (e.g., Medical Doctor, Doctor of Osteopathic Medicine, etc.), a physician's assistant, a nurse, a nurse practitioner, a medical imaging technician, a dentist, a chiropractor, etc. and includes any physician specializing in a relevant field (e.g., radiology).

The term "patient" generally refers to any animal, for example a mammal, under the care of a healthcare provider, as that term is defined herein, with particular reference to humans under the care of a primary care physician, oncologist, surgeon, or other relevant medical professional. For the purpose of the present application, a "patient" may be interchangeable with an "individual" or "person." In some embodiments, the individual is a human patient.

Additional Details Related to Computing Systems

Disclosed embodiments may comprise or utilize a special purpose or general-purpose computer including computer hardware, as discussed in greater detail below. Disclosed embodiments also include physical and other computer-readable media for carrying or storing computer-executable instructions and/or data structures. Such computer-readable media can be any available media that can be accessed by a general-purpose or special-purpose computer system. Computer-readable media that store computer-executable instructions in the form of data are one or more "physical computer storage media" or "hardware storage device(s)." Computer-readable media that merely carry computer-executable instructions without storing the computer-executable instructions are "transmission media." Thus, by way of example and not limitation, the current embodiments can comprise at least two distinctly different kinds of computer-readable media: computer storage media and transmission media.

Computer storage media (aka "hardware storage device") are computer-readable hardware storage devices, such as RAM, ROM, EEPROM, CD-ROM, solid state drives ("SSD") that are based on RAM, Flash memory, phase-change memory ("PCM"), or other types of memory, or other optical disk storage, magnetic disk storage or other magnetic storage devices, or any other medium that can be used to store desired program code means in hardware in the form of computer-executable instructions, data, or data structures and that can be accessed by a general-purpose or special-purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmission media can include a network and/or data links which can be used to carry program code in the form of computer-executable instructions or data structures and which can be accessed by a general purpose or special purpose computer. Combinations of the above are also included within the scope of computer-readable media.

Further, upon reaching various computer system components, program code in the form of computer-executable instructions or data structures can be transferred automatically from transmission computer-readable media to physical computer-readable storage media (or vice versa). For example, computer-executable instructions or data structures received over a network or data link can be buffered in RAM within a network interface module (e.g., a "NIC"), and then eventually transferred to computer system RAM and/or to less volatile computer-readable physical storage media at a computer system. Thus, computer-readable physical storage media can be included in computer system components that also (or even primarily) utilize transmission media.

Computer-executable instructions comprise, for example, instructions and data which cause a general-purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Disclosed embodiments may comprise or utilize cloud computing. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, wearable devices, and the like. The invention may also be practiced in distributed system environments where multiple computer systems (e.g., local and remote systems), which are linked through a network (either by hardwired data links, wireless data links, or by a combination of hardwired and wireless data links), perform tasks. In a distributed system environment, program modules may be located in local and/or remote memory storage devices.

Alternatively, or in addition, the functionality described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Application-specific Standard Products (ASSPs), System-on-a-chip systems (SOCs), Complex Programmable Logic Devices (CPLDs), central processing units (CPUs), graphics processing units (GPUs), and/or others.

As used herein, the terms "executable module," "executable component," "component," "module," or "engine" can refer to hardware processing units or to software objects, routines, or methods that may be executed on one or more computer systems. The different components, modules, engines, and services described herein may be implemented as objects or processors that execute on one or more computer systems (e.g., as separate threads).

One will also appreciate how any feature or operation disclosed herein may be combined with any one or combination of the other features and operations disclosed herein. Additionally, the content or feature in any one of the Figures may be combined or used in connection with any content or feature used in any of the other Figures. In this regard, the content disclosed in any one figure is not mutually exclusive and instead may be combinable with the content from any of the other Figures.

CONCLUSION

The present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached disclosure for purposes of illustrating embodiments of the present disclosure, it will be apparent to those skilled in the art that various changes in the methods, products, devices, and apparatuses disclosed herein may be made without departing from the scope of the disclosure or of the invention. Thus, while various aspects and embodiments have been disclosed herein, other aspects and embodiments are contemplated. All changes that come within the meaning and range of equivalency of the claims are to be embraced within their scope.

What is claimed is:

1. A computer-implemented method for preventing wrong-patient errors, comprising:
   receiving a selection of a current imaging subject, the current imaging subject being selected for a current image acquisition session comprising ci) capturing one or more current images of the current imaging subject utilizing at least a first image sensor system of a first imaging modality and (ii) capturing one or more additional current images of the current imaging subject utilizing at least a second image sensor system of a second imaging modality that is different from the first imaging modality, the second image sensor system being mounted to the first image sensor system;
   accessing a set of one or more previous images of a previous imaging subject, the one or more previous images of the previous imaging subject being associated with one or more image capture timepoints that temporally precede the current image acquisition session, the one or more previous images depicting the previous imaging subject according to at least the second imaging modality that is different from the first imaging modality;
   presenting the one or more previous images on a display system, the display system comprising a user interface associated with control of the second image sensor; and
   in response to determining that the previous imaging subject matches the current imaging subject based upon the one or more previous images of the second imaging modality, performing the current image acquisition session by (i) capturing the one or more current images of the current imaging subject utilizing at least the first image sensor system of the first imaging modality and (ii) capturing one or more additional current images of the current imaging subject utilizing at least the second image sensor system mounted to the first image sensor system.

2. The computer-implemented method of claim 1, wherein receiving the selection of the current imaging subject comprises receiving user input selecting the current imaging subject.

3. The computer-implemented method of claim 1, wherein accessing the set of one or more previous images of the previous imaging subject comprises accessing a data repository of imaging subjects based upon the selection of the current imaging subject.

4. The computer-implemented method of claim 1, wherein the one or more current images or the one or more previous images comprise one or more video frames.

5. The computer-implemented method of claim 1, wherein the user interface of the display system is further associated with control of the first image sensor system of the first imaging modality.

6. The computer-implemented method of claim 1, wherein the set of one or more previous images of the previous imaging subject further comprises at least one previous image depicting the previous imaging subject according to the first imaging modality.

7. The computer-implemented method of claim 1, wherein determining that the previous imaging subject matches the current imaging subject based upon the one or more previous images of the second imaging modality comprises receiving user input indicating that the previous imaging subject matches the current imaging subject.

8. The computer-implemented method of claim 1, wherein determining that the previous imaging subject matches the current imaging subject is further based upon one or more audio recordings of the current imaging subject.

9. The computer-implemented method of claim 1, further comprising associating the one or more current images with the previous imaging subject within a subject data repository.

10. The computer-implemented method of claim 1, wherein the first image sensor system is configured to be prevented from acquiring the one or more current images of the current imaging subject unless the previous imaging subject matches the current imaging subject.

11. The computer-implemented method of claim 1, wherein the first imaging modality comprises a medical imaging modality, the second imaging modality comprises a visible spectrum imaging modality, and the current imaging subject comprises a medical patient.

12. A computer-implemented method for preventing laterality errors, comprising:
    prior to performing a current image acquisition session of a structure using a first imaging modality, capturing one or more images of the structure using a second imaging modality that is different from the first imaging modality;
    accessing an indication of one or more intended structure attributes, the one or more intended structure attributes being selected to be embodied by the structure for the current image acquisition session;
    determining one or more imaged structure attributes by utilizing the one or more images of the structure of the second imaging modality as input to one or more artificial intelligence modules configured to determine structure attributes based upon input imagery, the one or more imaged structure attributes comprising output of the one or more artificial intelligence modules; and
    in response to determining one or more discrepancies between the one or more imaged structure attributes and the one or more intended structure attributes (i) preventing performance of the current image acquisition session and (ii) presenting a notification on a user interface.

13. The computer-implemented method of claim 12, wherein the one or more intended structure attributes comprise an intended laterality, and wherein the one or more imaged structure attributes comprise an imaged laterality.

14. The computer-implemented method of claim 12, wherein the one or more artificial intelligence modules comprise a convolutional neural network.

15. The computer-implemented method of claim 12, wherein performance of the current image acquisition session using the first imaging modality is conditioned on detecting no discrepancies between the one or more imaged structure attributes and the one or more intended structure attributes.

* * * * *